United States Patent
Meloen et al.

(10) Patent No.: US 6,761,890 B1
(45) Date of Patent: Jul. 13, 2004

(54) PEPTIDE, IMMUNOGENIC COMPOSITION AND VACCINE OR MEDICAL PREPARATION, A METHOD TO IMMUNIZE ANIMALS AGAINST THE HORMONE LHRH, AND ANALOGS OF THE LHRH TANDEM REPEAT PEPTIDE AND THEIR USE AS VACCINE

(75) Inventors: Robert Hans Meloen, Lelystad (NL); Hendrica Berendina Oonk, Lelystad (NL)

(73) Assignee: Pepscan Systems B.V., Lelystad (NL)

( * ) Notice: Subject to any disclaimer, the term of this patent is extended or adjusted under 35 U.S.C. 154(b) by 0 days.

(21) Appl. No.: 09/659,983

(22) Filed: Sep. 12, 2000

Related U.S. Application Data (63) Continuation-in-part of application No. 09/274,048, filed on Mar. 22, 1999, now Pat. No. 6,284,733, which is a continuation of application No. 08/981,557, filed on Dec. 5, 1997, now Pat. No. 5,885,966, which is a continuation of application No. PCT/NL96/00223, filed on Jun. 6, 1996, which is a continuation of application No. 08/477,298, filed on Jun. 7, 1995, now abandoned, which is a continuation of application No. 08/476,013, filed on Jun. 7, 1995, now abandoned.

(51) Int. Cl.[7] ........................ A61K 39/00; A61K 38/24; C07K 14/59; C07K 17/00
(52) U.S. Cl. .................... 424/185.1; 530/398; 530/399; 530/402; 530/403; 514/12; 514/13
(58) Field of Search ........................... 424/185.1, 184.1; 530/398, 399, 402, 403, 350, 313; 514/12, 13, 2

(56) References Cited

U.S. PATENT DOCUMENTS 5,573,767 A * 11/1996 Dufour et al. ......... 424/195.11

OTHER PUBLICATIONS

Alston–Mills et al. Production of Monoclonal Antibodies Against Avian LHRH–I. In Vitro Cellular and Developmental Biology vol. 25/No. 10 pp. 934–938 (1989).*
Wells, Additivity of Mutational Effects in Proteins. Biochemistry vol. 29/No. 37 pp. 8509–8517 (1990).*
Daniel et al. Mapping of Linear Antigenic Sites on the . . . A Combination of Nine Prediction Algorithms Fail to Identify Relevant Epitopes and Peptide Immunogenicity is Drastically Influenced by Nature of Protein Carrier. Virology 202 pp. 540–549 (1994).*

* cited by examiner

Primary Examiner—Yvonne Eyler
Assistant Examiner—Regine M. DeBerry
(74) Attorney, Agent, or Firm—TraskBritt (57) ABSTRACT

A peptide that comprises a modified tandem GnRH decapeptide sequence which allows for a testosterone level that is essentially non-detectable after vaccination with the peptide in a suitable dosage and/or allows for a an immunogenic response that allows for the effective discrimination between GnRH-I and GnRH-II and a method for the immunocastration of pigs.

11 Claims, 4 Drawing Sheets

PEPTIDE, IMMUNOGENIC COMPOSITION AND VACCINE OR MEDICAL PREPARATION, A METHOD TO IMMUNIZE ANIMALS AGAINST THE HORMONE LHRH, AND ANALOGS OF THE LHRH TANDEM REPEAT PEPTIDE AND THEIR USE AS VACCINE

This application is a continuation-in-part of application Ser. No. 09/274,048 filed Mar. 22, 1999, now U.S. Pat. No. 6,284,733, issued Sep. 4, 2001, which is a continuation of application Ser. No. 08/981,557 filed Dec. 5, 1997, now U.S. Pat. No. 5,885,966, issued Mar. 23, 1999, which is a continuation of PCT/NL96/00223, international filing date Jun. 6, 1996, which is a continuation of application Ser. No. 08/477,298 filed Jun. 7, 1995, now abandoned, which is a continuation of application Ser. No. 08/476,013 filed Jun. 7, 1995, now abandoned.

BACKGROUND OF THE INVENTION

1. Field of the Invention

This invention relates to a peptide suitable for eliciting an immune response against forms of Gonadotropine Releasing Hormone (GnRH) also referred to as Luteinizing Hormone Releasing Hormone (LHRH). The invention further relates to immunogenic compositions and vaccines, pharmaceuticals, and other medicinal preparations based on such a peptide. The invention further relates to the use of such a vaccine or medicinal preparation in a method of immunizing a mammal against GnRH to influence reproductive or behavioral characteristics of that mammal and in a method of improving the carcass quality of pigs. The invention also relates to a peptide suitable for eliciting a selective immunogenic response against GnRH-I or GnRH-II. Further the invention relates to antibodies against GnRH-I, to compositions comprising these antibodies and to the use of the peptides in pharmaceutical compositions or in the preparation for a medicament for the treatment of prostate cancer.

2. State of the Art

GnRH-I (in the literature generally depicted as GnRH) is a small 10 amino acid long peptide (decapeptide) from the hypothalamus. The amino acid sequence of GnRH-I (SEQ ID NO:1) can be represented by the following three-letter code:

pGlu-His-Trp-Ser-Tyr-Gly-Leu-Arg-Pro-Gly-NH$_2$ or the corresponding one letter code where pE is pyroglutamic acid and # is amide:

pE H W S Y G L R P G#                      SEQ ID NO:1

GnRH-I acts at the hypophysis to cause an increase in release of biologically active Follicle-Stimulating Hormone (FSH) and Luteinizing Hormone (LH) in the blood, which in turn stimulate the development of the tests in the growing made animal and the synthesis of male steroids. In the growing female animal the development of the ovaries is stimulated, as is the development of follicles within the ovary, synthesis of female steroids, and ovulation.

It is known that GnRH-I, if coupled to a carrier protein, can be used to vaccinate animals. Such a vaccination can be carried out for various reasons, all of which are connected with the natural function of the GnRH-I. As is known, a drastic reduction of LH and/or FSH in the blood inhibits the production of male steroids or androgens and sperm in the testis of the male and the formation of female steroids or progestagens and estrogens and follicle maturation in the ovary of the female. Such a reduction in the amounts of androgens, progestagens and estrogens in the blood, to a level comparable to that obtainable by removing the testes or ovaries via castration, can be achieved by effective immunization of the animal against GnRH-I. In male animals, in many cases the testes then appear to develop slowly or not at all, with no synthesis of androgens (male steroid hormones) and no formation of spermatozoa. In female animals the activity of the ovaria appears to diminish, with no synthesis of estrogens and progestagens (female steroid hormones), and inhibition of ripening of follicles and ovulation.

Recently it was reported that a second form of GnRH (GnRH-II) is present in primate brain (Lescheid et al. Endocrinol. 138(1997) 5618–5629) and a gene for this second GnRH molecule was cloned from a human genomic library (GnRH-II, amino acid sequence pEHWSHGWYPG# (SEQ ID NO:2)) (White et al., PNAS USA 95 (1998) 305–309). Mammalian GnRH-I (SEQ ID NO 1) is hardly expressed outside the brain. A few exceptions are known in this respect. GnRH I is present in the endometrium of women with a menstrual cycle (Casan et al. Fertil, Sateril, 1998, 70, 102–106) and is expressed during pregnancy in the human placenta (Kelly et al. DNA cell Biol. 1991, 10, 411–421). GnRH and mRNA was found in ovary, testis, thymus, placenta and hypothalamus of the rat (Oikawa et al., Endocrinology, 1990, 127, 2350–2356). Expression of GnRH was detected in immune tissue (spleen, thymus and lymphocytes) of pigs (Weesner et al., Life Sci, 1997, 61, 1643–1649).

GnRH-II is expressed in many tissues outside the brain, and is found is especially high concentrations in the kidneys, bone marrow and prostate. The presence of GnRH-II in diverse tissues other than the brain suggests that GnRH-II may have multiple functions. In addition, the strictly conserved structure of the GnRH-II peptide throughout diverse vertebrate species suggests that this neuropeptide possesses vital bioactivites. Until now, however, the functions of GnRH-II have been practically unknown. Several types of differential lymphocytes, such as T- and B-lymphocytes and mast cells, produce GnRH and GnRH-like peptides. Significant numbers of the latter cell type are present in kidney, bone marrow and prostate, perhaps contributing to the high GnRH-II expression in these tissues. GnRH II seems less involved in reproduction as compared to GnRH-I. In the hypogonadal mouse, mouse which lack the GnRH-I gene, GnRH-II producing cells are present in the same distribution as in normal mouse, but this is not sufficient to cause normal gonadal development in these mouse (Chen et al. FEBS Letters 435 (1998) 199–203). However, macaques in luteal phase of the menstrual cycle showed a marked increase in plasma luteinizing hormone concentrations after intravenous administration of GnRH-II, but this increase could not be induced during the mid follicular phase (Lescheid et al., Endocrinol. 138 (1997) 5618–5629.)

BRIEF SUMMARY OF THE INVENTION

The invention now provides the insight that by providing peptide sequences that allow discrimination between the different types of GnRH, more adequate and efficient use can be made of the variation or different in immunological response to the different types of GnRH. More particularly, the invention provides the insight that improvements in the efficiency and selectivity of the vaccines against GnRH-I can be achieved.

Immunization against GnRH-I is effective in neutralizing GnRH-I and results in reduced genadotropin levels and blocking of gonadal steroid synthesis. However, nothing in known about any physiological effects of the antibodies raised against GnRH-I on the function of GnRH-II. As GnRH-II is mainly synthesized and secreted in the kidneys antibodies raised against GnRH-I that cross-react with GnRH-II may affect kidney function. To obviate possible side effects of GmRH-I immunization on kidney function it would be desirable to direct the antigenic response of an immunocastration vaccine specifically toward GnRH-I and to avoid possible harmful side-effects due to neutralization of non-gonadal GnRH-II.

If the reproductive capacity alone, often with its accompanying sexual behavior, of a species needs to be annulled, it would be preferred to aim at an immunocastration vaccine specifically neutralizing GnRH-I. Hence the desired to come to a selective immunization against Gonadotropine Releasing Hormone(s), preferably selective against GnRH-I.

In veterinary medicine, 100% effective immunization against GnRH-I could be used for the sterilization of, e.g., small domestic animals such as male and female cats and dogs, or for the treatment of aggressiveness in male dogs and bulls, simply by vaccination instead of by drastic surgery such as castration or ovariectomy. Other conceivable reasons for immunization against GnRH-I are to prevent heat in female animals, such as dogs, cats and cows, and restlessness in male animals being fattened by slaughter.

In human health care immunization against GnRH-I and/or GnRH-II can be used in the treatment of prostatic cancer and breast cancer and, if required, in the treatment of some forms of pituitary carcinoma. In the case of prostate cancer it might be more desirable to neutralize both GnRH-I and GnRH-II, as the latter isoform is also highly expressed in prostate tissue.

Another use of a vaccine against GnRH-I is in the field of stock breeding, particularly the fattening of pigs of slaughter. The meat of male, sexually mature pigs (boars) has a typical odor, the so-called boar taint or boar odor. In the testes of the sexually mature pig, many C19-delta-16 steroids are formed which are stored in the fat tissue of the animal (Patterson, J. Sci. Food Agric. 19, 31–38 (1968); Brooks en Pearson, J. Anim. Sci. 62, 632–645 (1986); Claus, Zeitstchrift. Tierzüchtg. Züchtungsbiol. 93, 38–47 (1976); Claus, Acta Endocrinol. (Copenh.) 91, Suppl. 225, 432–433 (1979)). These steroids are mainly responsible for the formation of the disagreeable urine-like odor when the meat is heated (Fuchs, Swedish J. Agric. Res. 1, 233–237 (1971); Bonneau, Livest, Prod. Sci. 9, 687–705 (1982)). Owing to this unpleasant odor, meat of male sexually mature pigs is generally unsuitable for consumption and unfit for export. Because about 10% of the male slaughter pigs are already sexually mature before the slaughter time, this potentially entails a great loss for the pig farming industry.

In order to control and prevent these losses, nearly all male piglets are castrated when they are young, with a surgical procedure that is generally executed without any form of anaesthesia. Apart from the animal unfriendly aspect of such a castration, castration also leads to infections, growth inhibition, and a final carcass quality inferior to that of an intact animal, at least as long as that intact animal has not yet developed boar taint (Walstra, Livest. Prod. Sci. 1, 187–96 (1974)).

An animal friendly alternative consists in the reduction of the GnRH-I concentration in the pig pituitary by means of immunization against GnRH-I, the so-called immunocastration. This reduction in GnRH-I levels leads to a reduction in the concentrations of biologically active FSH and LH, which in turn will inhibit development of the testes in the growing animals and inhibit the synthesis of testicular steroids, including androstenone, testosterone and estrogens. This method prevents the occurrence of boar taint in male pigs at slaughter time and makes surgical castration unnecessary as androstenone levels are reduced to levels low or undetectable (Oonk et al., 1995, Livestock production Science 42, 63–71).

A strict requirement for an acceptable vaccine against boar taint is that in almost all pigs development of the testes is delayed to such an extent that boar taint will not have occurred at the time of slaughter, and that in the case that the vaccine does not reduce testis development in an animal, this can be easily detected in a too large testis size in comparison to successfully immunocastrated pigs.

In the existing literature and previous patent applications regarding the anti-fertility properties of vaccines against GnRH-I, the results of vaccinations often appear to be variable. In most of the described studies, either a small percentage of the vaccinated animals do not respond to the vaccination, or large doses of vaccine, multiple vaccinations or commercially unacceptable adjuvants are needed to produce the desired effect (Hoskinson et al., 1990, Austr. J. Biotech. 4, 166–170; Falvo et al., (1986) J. Anim. Sci. 63:986–994; Clarke et al., 1998, Endocrinology 139, 2007–2014; Adams T. E. and B. M. Adams, Feedlot performance of steers and bulls active immunized against Gonadotropine-Releasing Hormone, J. Anim. Sci. 1992, 70: 1691–1698; Brown et al., Immunization of sheep against GnRH-I early in life: effects of reproductive function and hormones in rams, Journal of reproduction and Fertility (1994) 101, 15–21; Ferro et al., Immunological castration using a Gonadotropine-releasing Hormone analogue conjugated to PPD, Food and agricultural immunology, 1995, 7, 259–272; U.S. Pat. No. 4,608,251; Int. patent appl. WO 88/05308).

Some studies suggested an efficacy of 100% of a vaccine against GnRH-I, but the vaccine was not tested in a large number of animals (Ladd et al. (1994), Development of an antifertility vaccine for pets based on active immunization against Luteinizing Hormone releasing hormone, Biology of Reproduction 51, 1076–1083; J. G. Manns and S. R. Robbins (1997). Prevention of boar taint with a recombinant based GnRH vaccine, In: Boar taint in entire male pigs, Proceedings of a meeting of the EAAP working group "Production and Utilisation of Meat from Entire Male Pigs", EAAP Publication No. 92, 137–140;); other studies report the efficacy of the vaccine as the mean value of the treated animals, since individual values did not show a clear difference between immunized and untreated controls (Bonneau et al., J. Anim. Sci. 72, 14–20 (1994); Hennesy et al., 1997. Elimination of boar taint; a commercial boar taint vaccine for male pigs. In: Bonneau, M., Lundström, K. and Malmfors, B. (Eds.), Boar taint in entire male pigs. Wageningen Pers, Wageningen, EAAP Publication No. 92, 141–145).

The difficulty in preparing this type of vaccines probably is caused by the phenomenon of tolerance. Self substances such as hormones are not recognised, as foreign but rather are tolerated by the immune system. Normally no antibodies are elicited against self substances. In order to a vaccine to be successful, it must be sufficiently foreign. Only when the vaccine is foreign enough will the immune system not tolerate the vaccine and the production of antibodies be induced. Conversely, however, the antibodies must still be capable of recognizing the hormone, and thus the vaccine cannot be too 'foreign'.

As these conditions appear to be mutually exclusive, it was not certain, until recently, if such substances could be prepared at all. One attempt to produce GnRH-like peptide vaccines consisted of the replacement of Gly at position 6 of the GnRH-I decapeptide by a dextrorotary amino acid (D-Tyrp; Chaffaux et al., Recueil de Médicine Vétérinaire 161 (2), 133–145, 1985). It was, however, demonstrated that a vaccine preparation containing this modified GnRH-peptide performed even less well than the normal GnRH-I decapeptide (European Patent application 464, 124 A).

Recently, we have shown definitively that it is possible to elicit an effective antibody response in all individuals vaccinated against GnRH-I (Meloen et al., Vaccine 12, 741–746 (1994)). In these experiments pigs were vaccinated twice with an GnRH-I vaccine that departs from the classical type of GnRH-I vaccine (GnRH-I coupled to a carrier protein, in Freund's adjuvant) namely the tandem-GnRH-I vaccine (European patent nr. 0464124). In this publication a peptide is described which is characterized in that is comprises at least 2 GnRH-I sequences in tandem (SEQ ID NO:3) according to the general formula $Z^1$-Glx-His-Trp$^1$-Ser-Tyr-Gly-Leu-Arg-Pro[-Gly-X-Gln-His-Trp$^2$-Ser-Tyr-Gly-Leu-Arg-Pro]$_n$-Gly-Z$^2$, in which amino acids are designated according to the three-letter code, $Trp^1$ and $Trp^2$ are tryptophan (trp) or formylated tryptophan ($N_{(indole)}$-formyl-tryptophan), n is a number having a value of at least 1, X is either a direct bond or a spacer group between the amino acids Gly and Gln, $Z^1$-Glx is either pGlu (pyroglutamic acid) or Gln having attached thereto a tail comprising one or more additional amino acids, and Gly-$Z^2$ is either Gly-NH$_2$ or Gly having attached thereto a tail comprising one or more additional amino acids. In this general formula, X may be a direct bond between the amino acids glycine and glutamine, i.e. these amino acids are interconnected directly without an intermediate link (via the normal peptide bond). The tandem-GnRH-I vaccine invention also comprises peptides in which the GnRH-I sequences are interconnected via spacers. The nature of the spacer group may vary greatly, from one or more amino acids to a shorter or longer hydrocarbon chain and other compound groups or molecules. In the above general formula, $Z^1$-Glx preferably stands for pGlu (pyroglutamic acid), but can also stand for Gln having attached thereto a tail comprising one or more additional amino acids, e.g., to be used for coupling of the peptide to a carrier protein. In the above general formula, Gly-$Z^2$ stands for, e.g., Gly-NH$_2$, or Gly having attached thereto a tail comprising one or more additional amino acids, e.g., to be used for coupling of the peptide to a carrier protein. Preferably, Gly-$Z^2$ stands for Gly-Cys-NH$_2$, the C terminal cysteine being added in connection with a possible coupling of the peptide to a carrier protein.

From WO 96/40755 it is known that the tandem-dimer principle applied to a variant of the GnRH-I molecule resulted in a vaccine that was highly effective in several mild adjuvants, namely Specol and a double oil emulsion, and was also effective in low doses. In this case, the variant of the GnRH-I molecule was formed by substitution of the sixth amino acid Gly of the decapeptide by a dextrorotary (D-) amino acid, D-Lys, following which the resulting peptide was dimerised and coupled to a common carrier compound, ovalbumine. Thus, whereas a vaccine using D-amino acid substitutions of Gly at positions 6 of the original and a single GnRH-I decapeptide with a D-amino acid decreased the immunogenicity as compared to the original GnRH-I sequence (Chaffaux et al., Recueil de Médicine Vétérinaire 161 (2), 133–145, 1985), such substitutions with a D-amino acid applied to a tandem-dimer GnRH-I vaccine were able to generate even ore immunogenic GnRH-I vaccine preparations, Nevertheless, the method for vaccination required a repeat dosage of the vaccine in order to be completely effective. The necessity of an additional booster dosage in order to achieve essentially 100% vaccination of mammals against GnRH-I is a disadvantage of the known peptides. We also found that in certain cases use of the (D-Lys$^6$)GnRH I tandem dimer (i.e. the GnRH I tandem dimer, with and without the D-Lys$^6$ replacement) resulted in very low but still measurable amounts of testosterone, which is undesirable and a disadvantage of the (D-Lys$^6$) GnRH I tandem dimer.

The present invention provides peptide sequences and that provide alternatives to the tandem D-Lys$^6$ GnRH-I when applied in vaccines that result in vaccines that are effective for immunocastration.

An aspect of the present invention is the determination of the extent to which the amino acids in the tandem GnRH-I sequence can be varied while the resulting substituted tandem GnRH-I is still able to produce an immunogenic response to GnRH-I sufficient for immunocastration. Thus, the invention provides for the generation of a peptide sequence that can induce the production of antibodies against GnRH-I, which are also sufficiently competitive, both in amount and activity.

A further aspect of the present invention is to provide to a peptide sequence that selectively induces the production of antibodies against GnRH-I, while inducing little or no immune response towards GnRH-II. A preferred embodiment thereof is a peptide sequence that not only selectively induces the production of antibodies against GnRH-I but is also effective in immunocastration, while an immune response to GnRH-II is reduced or absent.

The present inventors have found that in the tandem GnRH-I peptide sequence various amino acids can be replaced, resulting in a decreasing resemblance to the self-hormone while at the same time retaining or even increasing the ability of the peptide to elicit GnRH-I binding antibodies. Also, certain replacements of amino acids in the GnRH-I peptide sequence result in a selective immune response towards GnRH-I and to a reduced or absent immunoresponse towards GnRH-II.

In an aspect of the invention, certain modified tandem GnRH-I peptide sequences provide for vaccines that are not only capable of reducing testes growth in male animals but are also capable of essentially reducing testosterone levels to a degree that they can not be determined by conventional techniques.

Further, vaccines prepared from the these peptide-sequences express an activity that in most cases eliminated the need for the second booster immunization, as with the conventional D-Lys$^6$ tandem GnRH-I, to achieve essentially 100% activity. An activity or efficacy of 100% in the terms of the present invention is defined as a testosterone level that is essentially undetectable with conventional techniques after a single vaccination.

One of the most notable features of the present invention is that antibodies raised by these alternative GnRH vaccines discriminate between GnRH-I and GnRH-II. Thus peptides according to the invention express an increased or retained activity against GnRH-I, while at the same time a reduced or absent immune response to GnRH-II is found. This allows for the development of peptides that express an inverse effect, that is, they express an increased or retained activity against GnRH-II while at the same time expressing a reduced or absent immune response against GnRH-I.

The invention relates in one aspect to a peptide that comprises a modified tandem GnRH-I decapeptide sequence whereby vaccination with the peptide in a suitable dosage allows for a testosterone level that is essentially non-detectable.

The invention also relates to a peptide that comprises at least two coupled GnRH-I decapeptide sequences, optionally coupled through a spacer, which allows for an immunogenic response that allows for the effective discrimination between GnRH-I and GnRH-II.

The peptides according to the invention are sufficiently like the hormone but at the same more 'foreign' to the immune system and have an increased capability to induce the production of antibodies directed against the hormone.

A feature of the invention is that individual tandem units can be dimerised to further enhance its immunogenicity without losing the possibility of coupling the peptide or peptide composition to a carrier compound protein.

The techniques for dimerisation and coupling of the tandem to a carrier similar to those described in WO 96/40755 may be used. It is also envisioned that peptides containing only a portion of the GnRH-I or II peptide sequences can be used in the present invention. Examples thereof are nonapeptides and undecapeptides.

The linkers for use in the peptides according to the invention can be selected from the linkers described elsewhere in this application or linkers and such as Linkers are used for coupling two or more dimerised peptide sequences. The amino acid which is used to replace the amino acid in the tandem peptide sequences is preferably an amino acid which is a relative simple one, such as alanine. In a preferred embodiment therefor the different amino acid is alanine. Other amino acids can also be used to replace the amino acid in the tandem decapeptide sequence. Preferably only conservative replacements are carried out. Conservative replacements are amino acid substitutions in which bulky amino acids are replaced by bulky amino acids, aromatic amino acids by aromatic amino acids etc. These concepts are well known to those skilled in the art.

Spacers can be placed between the peptides according to the invention. This allows for the formation of multimers. Suitable spacers are known in the art.

DESCRIPTION OF THE DRAWINGS

FIG. 1A–C Competition for binding of iodinated GnRH with antiserum by GnRH (open circles), GnRH-II (solid circles), control peptide (solid squares) and no peptide (asterix). Serum is diluted 1/10000 and increasing peptide concentrations (0.25, 2.5, 25 pmol) per well were added. In graphs A–C sera with increasing binding capacity for GnRH-II are shown. Horizontal axis: amount of peptide (pmol per well); vertical axis: Binding capacity (counts per minute).

FIG. 3A–D: Percentage of maximum binding of antiserum to iodinated GnRH after competition with GnRH-I (dark bars) or GnRH-II (light bars) for antiserum against pEIA collected at 7 wpv (A), and at 10 wpv (B) and for antiserum against S4A collected at 7 wpv (C), and at 10 wpv (D). Antiserum obtained at 7 wpv and at 10 wpv was tested in an 1/2000 and 1/1000 dilution respectively. 25 pmol peptide for competition was added per well. Horizontal axis: animal identification #; Vertical axis: percentage of maximum binding.

DETAILED DESCRIPTION OF THE INVENTION

In a feature of the invention, the peptides according to the invention have the general formula given by (SEQ ID NO:4), or by the following one-letter code:

pEHWSYkLRPGQHWSYkLRPGC#

In this general formula Q stands for Gln and may be preceded by X were X stands for a spacer. Several of these amino acids have been replaced with other amino acids. In the formulas the position of the substitution is depicted bold and <u>underscored</u>. Capital letters stand for Levorotatory amino acids. Lower case letters stand for Dextrorotatory amino acids, e.g. K: L-Lys; k:D-Lys. Subsequently their immunogenic response has been determined when coupled to a carrier, generally ovalbumine, but other carriers such as KLH, BSA can be used.

It will be clear that the sequence of the GnRH-II peptide (SEQ ID NO:2) determines which of the amino acids can be replaced in such manner that an effective discrimination based on the immune response to still possible between the two sequences GnRH-I, and GnRH-II.

To determine whether antibodies raised by the GnRH vaccines according to the present invention discriminated between GnRH-I and GnRH-II, a GnRH antibody binding assay was performed in order to determine whether antibodies raised against GnRH-I-tandem dimer peptide or its alanine replacement analogs bind to GnRH-II or lack binding to GnRH-II. Serum dilutions were preincubated with either GnRH-I GnRH-II, a control peptide or no peptide. Next iodinated GnRH-I was added to compete with the preincubated peptides for binding to the antibodies.

This procedure was performed for serum collected before and after booster immunization, as specificity of the antibodies may increase after booster immunization.

When the peptides according to the invention were used as the conjugate with ovalbumine (OVA-conjugate) and compared to controls, all showed effectiveness in the immunocastration of young male pigs. Comparison with the known G6k-GnRH tandem dimer OVA conjugate (see, Table 1), showed that the peptides according to the invention presented comparable or similar effectiveness even though their resemblance to the 'self'-hormone GnRH-I has decreased. The peptides according to the invention give an immunogenic response that allows for the effective discrimination between GnRH-I and GnRH-II. These peptides resulted in small testes and low testosterone levels. More specifically, the peptides expressing a low testes weight and a low testosterone level are R8A, G10A and S4A. The preferred peptides based on immunological selectivity between GnRHI and GnRH II are S4A and pE1A.

In a preferred embodiment, the peptide is selected from the group consisting of pEHWAYkLRPGQHW AYkLRPGC# (SEQ ID NO:5), pEHWSYkL APGQHWSYkLAPGC# (SEQ ID NO:6) and pEH-WSYkLRPAQHWSYkLRPAC# (SEQ ID NO:7). It is more preferably selected from the group consisting of pEH-WSYkLAPGQHWKYkLAPGC# (SEQ ID NO:6); and pEHWSYkLRPAQHWSYkLRPAC# (SEQ ID NO:7).

In the peptides according to the invention, dimerisation of the tandem units can for example take place via the carboxyl-terminus or via the amino-terminus. Two tandem units may for instance be dimerised by means of a disulfide or thioether bridge. To dimerise the tandem sequences the Cys at position 21 can be used, or Cys can be synthesized before the glutamic acid at position 1. Other methods to dimerise or multimerise the GnRH-tandem units can also be found in the prior art. If the Cys at position 21 is involved in the dimerisation and accordingly not available for coupling, it is likewise possible to use another amino acid of the tandem that can be coupled. If the dimerisation or multimerisation results in the loss of accessible sites where a carrier compound can be conjugated, it is sufficient to restrict the choice of replacement amino acids to an amino with an appropriate side chain. Such a replacing amino acid can be, for example, L or D-Lys, L or D-Glu or another amino acid containing a side chain that allows coupling to a carrier compound. Both L- and D- substitutions have been tested and found to have the same effect.

More in particular, an example of such a preferred peptide according to the invention, a D-Lys⁶-tandem-GnRH dimer (SEQ ID NO:8) according to the following formula:

```
        1                      21
   #EHWSYkLRPGQHWSYkLRPGC
                              |
   #EHWSYkLRPGQHWSYkLRPGC
        22                     42
```

In this example of an embodiment of the invention it is possible to replace one of the amino acids of the tandem-dimer by another amino acid.

Other peptides or peptide sequences or coupled peptide sequences in which monomerised, dimerised or multimerised GnRH tandem units are present that contain amino acid substitutions are also part of the invention.

The invention further provides a composition which comprises a peptide brought into an immunogenic form. As a skilled worker knows, there are different methods of producing an immunogenic form of a substance which is in itself not immunogenic. One possibility is to couple a peptide according to the invention to a suitable carrier protein. A suitable carrier protein is ovalbumin, KLH or BSA. In a tandem peptide a cysteine at the—or C-terminus can be suitably used for a chemical coupling. In the tandem-dimer peptide, coupling can also be performed using the plain or the modified side chain of (D-) lysine, (D-) glutamine, or any other modified amino acid replacing amino acids of the peptide sequence. Suitable coupling methods and carrier proteins are well known to those of ordinary skill in the art.

According to the invention, there is preferred a composition which is characterized in that it comprises an immunogenic conjugate of a protein, such as ovalbumine, and a peptide or peptide composition.

A composition according to the invention can be used in the form of a vaccine. To this end the composition can be produced in a form that is suitable for administration. By administration of a vaccine according to the invention, an immunogenic response against GnRH is generated, preferably an immunogenic response against GnRH-I.

The invention therefore also provides a method of immunizing a mammal against GnRH-I, through vaccination of the mammal with a vaccine according to the invention. In a preferred embodiment, the invention provides a method of selectively immunizing a mammal against GnRH-I, with a vaccine according to the invention.

Of course, the vaccine preparation according to the invention can be combined with at least one immunoadjuvant. Suitable immunoadjuvants are known to those skilled in the art. A preferred adjuvant according to the invention can be Specol or a double oil emulsion, but other adjuvants that elicit no or only mild side-reactions can be used as well. The invention can be used in methods for immunizing individuals selected from a wide range of vertebrates, and particularly mammals, against GnRH-I. In a preferred embodiment of the invention, the vaccine can be administered in a single dose, which has the same efficacy as the presently known vaccines which must be administered in two-dose form. Immunization against GnRH-I, preferably selective, could for instance be used for the sterilization of, e.g., small domestic animals such as male and female cats and dogs, or for the treatment of aggressiveness in male dogs and bulls. Other conceivable reasons of immunization against GnRH-I with the present invention are preventing heat in female animals such as dogs, cats and cows, and preventing or treating restlessness in male animals being fattened for slaughter. In human health care, immunization against GnRH, preferably selective against either GnRH-I or GnRH-II, can be used in the treatment of prostate cancer and breast cancer and if required, in the treatment of some forms of pituitary carcinoma.

A preferred embodiment is a method of improving the carcass quality of pigs, wherein the pigs are vaccinated with such a vaccine preparation according the invention. The invention is illustrated in the following experimental part.

I. Immunocastration of pigs

MATERIALS AND METHODS

Materials

Acetonitrile (ACN) was HPLC-S gradient grade, N-methylpyrrolidone (NMP), diisopropylethylamine (DIEA) dimethylformamide (DMF), trifluoroacetic acid (TFA) and piperidine were peptide synthesis grade and were all obtained from Biosolve (Valkenswaard, NL). N-hydroxybenzotriazole (HOBt) and 2-(1H-benzotriazol-1-yl-1,1,3,3-tetramethyluronium hexafluorophosphate (HBTU) were obtained from Richelieu Biotechnologies Inc. (Hamon Canada). Benzotriazol-1-yl-oxy-tri-pyrrolidino-phosphonium hexafluorophosphate (PyBOP) was obtained from Novabiochem (Laufelfingen, Switserland). Thioanisole (TA), ethanedithiol (EDT), dimethylsulfoxide (DMSO), pentane and dimethylaminopyridine (DMAP) were pro-analysis grade and were obtained from Merck (Darmstad Germany). Diethylether was purified over a column of activated, basic aluminum oxide before use. Amino acid derivatives and resins were obtained from Bachem Feinchemicalien AG (Bubendorf, Switserland).

Multiple Peptide Synthesis (MPS)

A Hamilton Microlab 2200 was programmed to deliver washing solvents and reagents to a rack with 40 individual 4 ml columns with filter, containing 30 mmol of resin for peptide synthesis. The columns were drained after each step by vacuum. The coupling cycle was based on Fmoc chemistry using double coupling steps:

1. NMP wash (1 ml)
2. 30% (v/v) piperidine/NMP (3 min, 0.5 ml)
3. 30% (v/v) piperidine/NMP (17 min, 0.5 ml)
4. NMP wash (5×1 ml)
5. double coupling (2×30 min)
6. NMP wash (2×1 ml)

Coupling step: Fmoc-amino acid in NMP (0.4 M, 0.25 ml), HBTU/HOBT (0.45 M, 0.22 ml) in DMF, and DIEA (2 M, 0.2 ml) in NMP were transferred to the reaction vessel and allowed to react for 30–50 min. The reaction mixture was drained and the coupling procedure was repeated once.

After coupling of the last amino acid, the Fmoc group was cleaved with 30% piperidine/NMP, the peptides were washed, acetylated in 30 min. using NMP/acetic anhydride/DIEA 10/1/0.2, washed again, and dried. The peptides were deprotected and cleaved in 2 hr in a mixture of 1.5 ml of TFA/phenol/TA/water/EDT 10/0.75/0.5/0.5/0.25 (reagent K). The cleavage mixture was filtered, the resin was washed with 0.5 ml TFA, and the peptide was precipitated by adding 13 ml pentane/diethylether 1/1. After centrifugation, the precipitate was extracted again with pentane/diethylether. The precipitate was dried, dissolved in ACN/water 1/1 and lyophilised. This procedure yields, depending on molecular weight, 25 to 70 mg of peptide.

Peptide sequences synthesized in single letter amino acid code are summarized in Table 1.

TABLE 1

Amino acid sequence in single letter code of peptides synthesized

| peptide | amino acid sequence |
| --- | --- |
| G6k-GnRH-tandem | pEHWSYkLRPGQHWSYkLRPGC# (SEQ ID NO: 9) |
| PE1A-G6k-GnRH-tandem | *AHWSYkLRPGAHWSYkLRPGC# (SEQ ID NO: 10) |
| S4A-G6k-GnRH-tandem | pEHWAYkLRPGQHWAYkLRPGC# (SEQ ID NO: 5) |
| Y5A-G6k-GnRH-tandem | pEHWSAkLRPGQHWSAkLRPGC# (SEQ ID NO: 11) |
| L7A-G6k-GnRH-tandem | pEHWSYkARPGQHWSYkARPGC# (SEQ ID NO: 12) |
| R8A-G6k-GnRH-tandem | pEHWSYkLAPGQHWSYkLAPGC# (SEQ ID NO: 6) |
| P9A-G6k-GnRH-tandem | pEHWSYkLRAGQHWSYkLRAGC# (SEQ ID NO: 13) |
| G10A-G6k-GnRH-tandem | pEHWSYkLRPAQHWSYkLRPAC# (SEQ ID NO: 7) | pE = pyroglutamic acid; * = acetyl; # = amide; k = d-lysine; G6k = Gly on position 6 in the native GnRH sequence substituted by d-Lysine Analytical HPLC For analysis of peptides, we used a LC-MS (electrospray) system, which consists of two Waters pumps model 510, a Waters gradient controller model 680 a Waters WISP 712 autoinjector, and a Waters 991 photodiode array detector. The mass spectrometer was a Micromass Quattro II sq, which was used in positive ion mode. Products were analyzed in a linear gradient from 10% ACN/water with 0.05% TFA to 70% ACN/water with 0.05% TFA in 30 min on a Waters Delta Pak C18-1000Å (3.9×150 mm, 5 mm) column at 1 ml/min at 215 nm. All products were between 40–70% pure according to the peak area.

Dimerisation

Crude products were dimerised by dissolving the products in 20% DMSO in water. The pH was adjusted to 5–6 with 1% $NH_4HCO_3$, maintaining a clear solution. Correction of pH was done with 1% acetic acid. After stirring at room temperature for at least 5 h, the products were stored at −20° C. until purification.

Preparation HPLC

Peptides purifications were carried out using a Waters Prep 4000 liquid chromatograph, equipped with a Waters RCM module with two PrepPak cartridges plus guard cartridge (40×210 mm or 25×210 mm) filled with delta-Pak C18-100Å (15 mm) material. In general, purifications were run using the same eluents as in analytical HPLC, but at a gradient speed of 0.5% ACN/min and a flow rate of 40 or 100 ml/min. Peptides were detected at 215–230 nm using a Waters 486 spectrophotometer with a preparative cell. The peptides were lyophilised and purity was determined to be at least 90%.

Conjugate Preparation

For conjugation via N-ethyl-N=-(3'-dimethylaminopropyl)carbodiimide hydrochloride ("EDC") to chicken egg albumin ("OVA") an equal weight of both the peptide and the carrier protein were dissolved separately in milliQ water and both solutions were mixed well. Next a 10-fold excess, based on weight equivalents, of EDC was dissolved in milliQ water. Subsequently, this solution was slowly added to the solution of peptide/OVA under continuous stirring, pH of this final solution is 5. After at least 6 h slowly shaking the product was dialyzed (MV cut-off 10,000) against a 300 times excess of milli Q water for two days. Water was refreshed twice a day. The loading was calculated from comparative amino acid analysis of the conjugate and the carrier protein. Amino acid analysis was performed using a Waters Pico-Tag system, after hydrolysis in a Pico-Tag workstation using 6N HCl at 150° C. for 1 h, and derivatisation with phenyl isothiocyanate.

According to the amino acid analysis the conjugates contained between 0.3 and 0.5 mg of peptide per mg of carrier protein, with exception of the P9A-G6k-GnRH-tandem-dimer conjugate which only contained 0.16 mg peptide per mg ovalbumine.

The G6K-GnRH-tandem-dimer OVA conjugate is abbreviated by G6k-TD. The conjugates with alanine substitutions are abbreviated by the amino acid in the native GnRH sequence that is replaced, it position and an A for the Alanine replacement. For example pE1A-G6k-GnRH-tandem-dimer OVA conjugate is pE1A.

Emulsion Preparation

Specol (Special Oil Phase, ID-DLO, Lelysad, The Netherlands) consisting of two detergents n a light mineral oil was used as oil phase (Bokhout et al., 1981). The water-in-oil-(WIO)-emulsions were prepared using an Ultra Turrax (Janke and Kunkel, Staufen, Germany) with a stirring bar i 25 mm. The oil phase Specol (5 parts v/v) was brought into a 25 ml glass vessel and the water phase (4 parts v/v) consisting the conjugate in milli Q water was slowly added while the emulsion was stirred. After the water phase was added, the emulsion was stirred for half a minute at the same rotation speed (15000 rpm). Emulsions were stored overnight at 4° C. to check stability and were administered to the animals the next day.

Animals

Male piglets, approximately 10 weeks of age, were involved in this experiment. The crossbred piglets were housed in half slatted pens and were given ad libitum access to feed and water.

Immunization

The piglets were randomly assigned to the treatments, 6 or 7 piglets per treatment. All animals were injected with 2 ml emulsion containing the dimerised tandem GnRH conjugates (i.e. 62 mg peptide) or an emulsion without antigen. Injections were administered intrasmuscularly in the neck at the start of the experiment (day 0) and 7 weeks later (7 wpv). Thirteen weeks after initial immunization (13 wpv) all animals were slaughtered.

Measurements and Blood Sampling

Animals were weighed at day 0 and 7 and 13 wpv. Testis sizes were determined by measuring testis length with a vernier calipers at day 0, and 7, 100 and 13 weeks thereafter. Testis sizes were recorded as average of both testicles.

Blood samples were taken via puncture of the vena jugularis on the same days testis sizes were measured, and also 4 weeks after the initial immunization. Blood samples were kept overnight at 4° C. and the next day serum was obtained by centrifugation (1500 g, 15 min). Serum samples were stored at −20° C. until assayed.

Evaluation After Slaughter

After slaughter testes were removed, dissected free of epididymes and weighted. Testes weights were recorded as average of both testicles.

Peptide Antibodies

Antibodies to the peptides used for immunization were determined with an ELISA. Peptides were coated in the wells of a microtitreplate using glutardialdehyde (GDA). GDA was coated to the surface of the wells by incubation with 0.2% GDA in 0.1 M phosphate buffer (pH 5) for 4 hours at room temperature. Plates were rinsed 3 times for 10 minutes with 0.1 M phosphate buffer (pH 8). One microgram peptide in 100 ml phosphate buffer (0.1 M, pH 8) was coated per well by incubating for 3 hours at 37° C. Plates were stored at −20° C. until used. Thawed plates wee rinsed 3 times for 10 minutes with milli-Q water containing 8.2 g NaCl, 1.15 g $Na_2HPO_2 \cdot 2H_2O$, 0.20 g $NaH_2PO_4 \cdot 2H_2O$ and 5 ml of a 10% Tween 80 solution in water per liter water.

Serial serum dilutions of the antipeptide sera were allowed to react with the coated peptides for 1 hour at 25° C. After rinsing for 3 times 10 minutes goat-anti-pig IgG coupled to horseradish peroxidase (Dako, Glastrup, Denmark) was introduced as second antibody for 1 hour and ABTS (Boehringer, Mannheim, Germany) ((250 ml (2 g/100 ml) in 10 ml substrate buffer to which 20 ml $H_2O_2$ (3% solution)) was used as substrate. Absorption was measured at 405 nm.

GnRH Antibodies

Antibodies to GnRH were determined as described by Meloen et al. (Vaccine 12, 741–746 (1994)). Serial dilutions of the pig antisera were allowed to bind to $^{125}$I-GnRH. Titers are expressed as percentage binding of $^{125}$I-GnRH at a given serum dilution.

Testosterone

Testosterone levels in serum were determined using a Coat-a-Count kit purchased from DPC laboratories, Log Angeles, Calif.

RESULTS

Testis Size and Testis Weight

Seven weeks after the first immunization, immunocastration effects already could be observed by measuring testicle sizes. Three treatments (R8A, G10A and G6k-TD) showed hardly any increment (<10 mm) of average testis size at time of booster. These treatments were successful with testis weights at slaughter being 70 germs or less. Other treatments that were effective in terms of low testes weights are pE1A and S4A, while in group Y5A, L7A, and P9A, 2, 1 and 1 animals did not respond to the immunization respectively (Table 2). Individual tests weight of immunocastrated animals did not exceed 70 grams, resulting in a clear different between immunocastrated and not immunocastrated animals.

TABLE 2

Effectiveness of the different treatments according testis weight (g)

| treatment | individual testis weight (g) | testis weight (g) (median (range)) | number responders/ total number |
|---|---|---|---|
| G6k-TD | 10, 10, 10, 12, 16, 70 | 11 (10–70) | 6/6 |
| pE1A | 16, 18, 33, 36, 53, 55, 65 | 36 (16–65) | 7/7 |
| S4A | 10, 14, 15, 36, 40, 43, 69 | 36 (10–69) | 7/7 |
| Y5A | 15, 19, 34, 44, 69, 210, 235 | 44 (15–235) | 5/7 |
| L7A | 12, 13, 15, 20, 24, 29, 195 | 20 (12–195) | 6/7 |
| R8A | 10, 10, 12, 15, 17, 19, 19 | 15 (10–19) | 7/7 |
| P9A | 8, 9, 20, 23, 31, 57, 300 | 23 (8–300) | 6/7 |
| G10A | 11, 13, 14, 14, 15, 30, 39 | 14 (11–39) | 7/7 |
| Controls | 150, 173, 204, 206, 236 | 204 (150–236) | 0/5 |

Antibody Response

Mean antibody titers against the peptides used for immunization are given in table 3. Mean antibody titer of pigs treated with H2A and P9A are lower than peptide antibody titer of the other treatments.

Antibody titers of individual animals against the different peptides ranged from 2 to 4. Within a treatment animals that were not immunocastrated showed the lowest antipeptide titer. Animals treated with H2A and $W_3A$ were not immunocastrated, but significant antipeptide titers were present.

GnRH antibody binding percentages at ½000 serum dilution were undetectable or lower in H2A and W3A groups. However at a ½000 serum dilution antibodies were detectable in sera of all animals of group H2A and three animals of group W3A.

Animals with low average GnRH antibody titers were not immunocastrated. High antibody titers did always result in successful castrated animals. Testicle weight of animals with intermediate antibody titers varied from 15 to 300 gram.

Average GnRH antibody titers per treatment showed a clear relation with testis weight (median) per treatment (Table 3).

Testosterone

Testosterone levels of all successful treated animals were low and decreased after second immunization. However a majority (n=31) of the animals reflected a castration effect as early as four weeks after initial immunization by showing undetectable testosterone levels. Testis weight of these animals varied from 8–36 grams.

The majority of the animals were thus effectively immunized after the administration of a single dose.

Although testosterone levels at slaughter were low for all immunocastrated animals, two animals with testes weights of 65 and 70 grams had significant serum testosterone levels of 3.80 and 1.18 pmol/ml respectively.

The peptides that resulted in low testes weight combined with undetectable testosterone levels are considered the most effective peptides for the immunocastration of pigs. These peptides are S4A, R8A and G10A.

Testosterone levels at slaughter of pigs that were no immunocastrated animals varied between 0.46 and 48.91 pmol/ml.

TABLE 3

Effect of different treatments on mean testis weight, peptide antibody titer, GnRH antibody binding percentage and LH and testosterone levels in serum.

| Treatment | testis weight (median range) | anti peptide titer at 10 wpv | GnRH binding (average) | testosterone (pmol/ml) at 13 wpv median (range) |
|---|---|---|---|---|
| G6k-TD | 11 (10–70) | 3.32 | 17.2 | n.d. (n.d.–1.18) |
| pE1A | 36 (16–65) | 3.24 | 15.7 | n.d. (n.d.–3.80) |
| S4A | 36 (10–69) | 3.19 | 16.9 | n.d. (n.d.) |
| Y5A | 44 (15–235) | 2.92 | 11.3 | n.d. (n.d.–9.44) |
| L7A | 20 (12–195) | 3.52 | 17.6 | n.d. (n.d.–48.91) |
| R8A | 15 (10–19) | 3.34 | 17.7 | n.d. (n.d.) |
| P9A | 23 (8–300) | 2.62 | 15.8 | n.d. (n.d–11.57) |
| G10A | 14 (11–39) | 3.19 | 17.6 | n.d. (n.d.) | wpv = weeks post vaccination, n.d. = not detectable

II. Replacement of D-amino acid with L-amino acid

D-lysine (k) at positions 6, 16, 27, and 37 in a tandem dimer is replaced by an L-lysine (K) and the resulting peptide tested (Table 4).

G6k-GnRH-tandem: pEHWSYkLRPGQHWSYkLRPGC# (SEQ ID NO:9)

G6K-GnRH-tandem: pEHWSYKLRPGQHWSYKLRPGC# (SEQ ID NO:14)

TABLE 4

| treatment | testis weight (g) median (range) | number res- ponders/ total | anti peptide titer at 10 wpv | GnRH- binding (average) | testoste- rone in pmol/ml, at 13 wpv, (median) |
|---|---|---|---|---|---|
| G6k-TD | 11 (10–70) | 6/6 | 3.32 | 17.2 | n.d. |
| G6K-TD | 21 (9–175) | 5/6 | 2.70 | 15.6 | n.d. |
| Controls | 204 (150–236) | 0/5 | n.d. | n.d. | 2.05 | n.d.: not detectable.

Replacement of D-lysine by L-lysine does not alter efficacy of the vaccine antigen.

III. Discrimination between GnRH-I and GnRH-II

An GnRH antibody binding competitive radioimmunoassay was performed in order to determine whether antibodies raised against G6k-GnRH-tandem (SEQ ID NO:9) dimer peptide or its alanine replacement analogs bind to GnRH-II or lack binding to GnRH-II. Serum dilutions were preincubated with either GnRH-I, GnRH-II, a control peptide or no peptide. Next iodinated GnRH-I was added to compete with the preincubated peptides for binding to the antibodies.

This procedure was performed for serum collected before and after booster immunization, as specificity of the antibodies may increases after booster immunization due to antibody maturation.

Materials and Methods

Serum samples of the 10 wpv bleeding (3 weeks post booster immunization) were diluted 1/10000 in PBS with 0.4% BSA (dilution buffer). Fifty µl serum dilution was put in microwell plates and 25 µl peptide solution (0, 0.25, 2.5 or 25 pmol peptide in dilution buffer per well) was added. This mixture was allowed to incubate for 24 hours at 4° C. The next day 25 µl iodinated GnRH (approximately 13000 cpm) was added and after overnight storage (4° C.) unbound peptide was separated from bound peptide with charcoal. After centrifugation supernatant was separated, counted and the percentage iodinated GnRH bound to the antibodies was calculated.

Antibodies collected after the first immunization (7 wpv) were tested in a 1/2000 serum dilution and only one peptide dilution was tested (25 pmol/well).

Results

Figure 1:
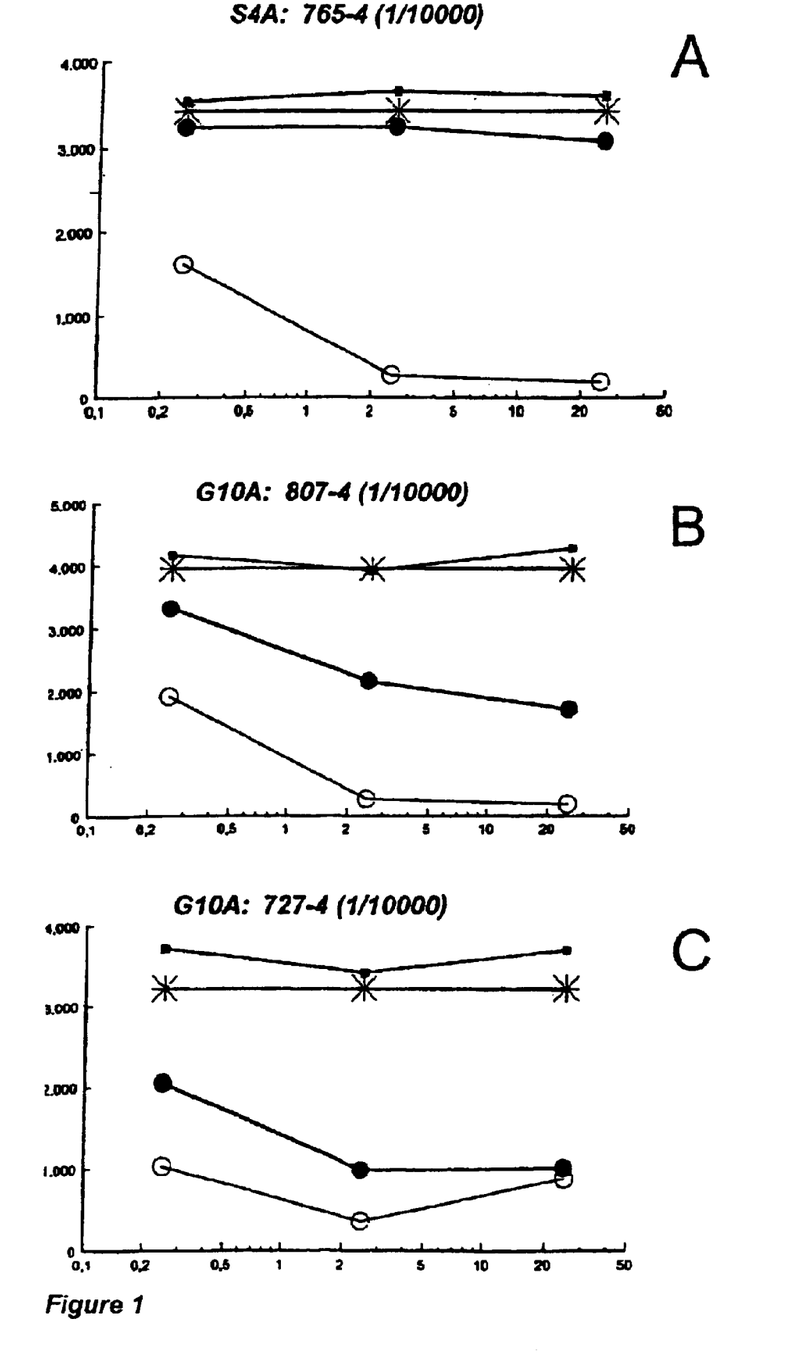

Binding of iodinated GnRH at a 1/10000 serum dilution was observed for the sera of all treatments except for H2A and W3A sera. Competition with GnRH-I results in a dramatic reduction of binding of iodinated GnRH to the antiserum (see FIG. 1). At the sera dilution we tested, inhibition of binding of iodinated GnRH by GnRH-I was dose dependent for most sera. As expected, none of the antisera bound to the control peptide.

Figure 2:
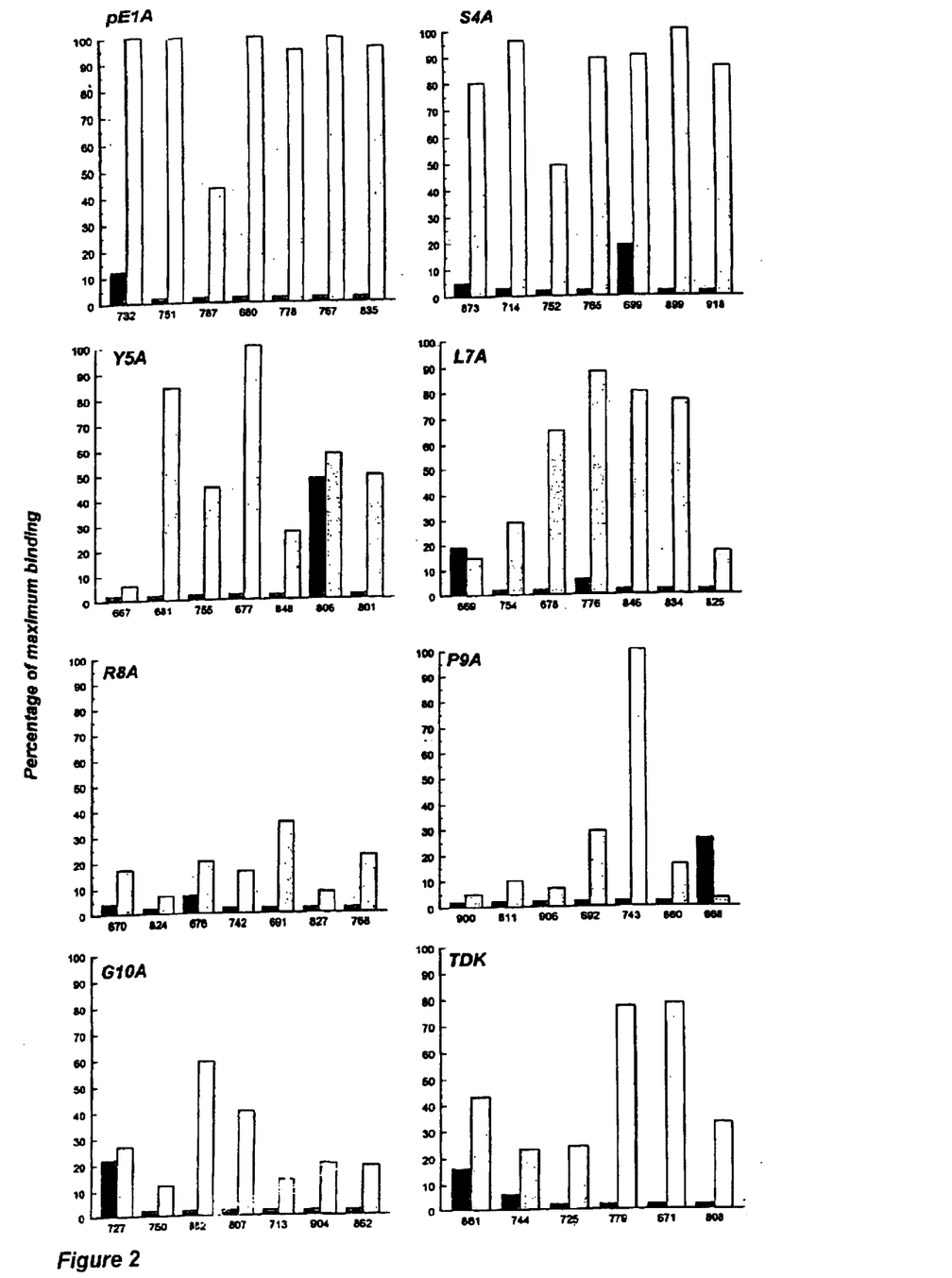
FIG. 2: Percentage of maximum binding of antiserum to iodinated GnRH after competition with GnRH-I (dark bars) or GnRH-II (light bars) for sera obtained after immunization with the peptides indicated in the left top corner of each graph. Antiserum obtained 3 weeks after boosterimmunisation was diluted 1:10000 and peptides for competition were added in 250 nmol per liter. Horizontal axis:animal identification #; Vertical axis: percentage of maximum binding.

Competition by GnRH-II for antibody binding to iodinated GnRH resulted in a reduced binding in all sera of R8A and G10A treatments, in most of the sera of treatments P9A and TDK and in half of the sera of treatments Y5A and L7A (see FIG. 2). However, antibodies of substantially all animals of the pEIA and the S4A group completely lacked binding to GnRH II, and were thus specific for GnRH I.

Figure 3:
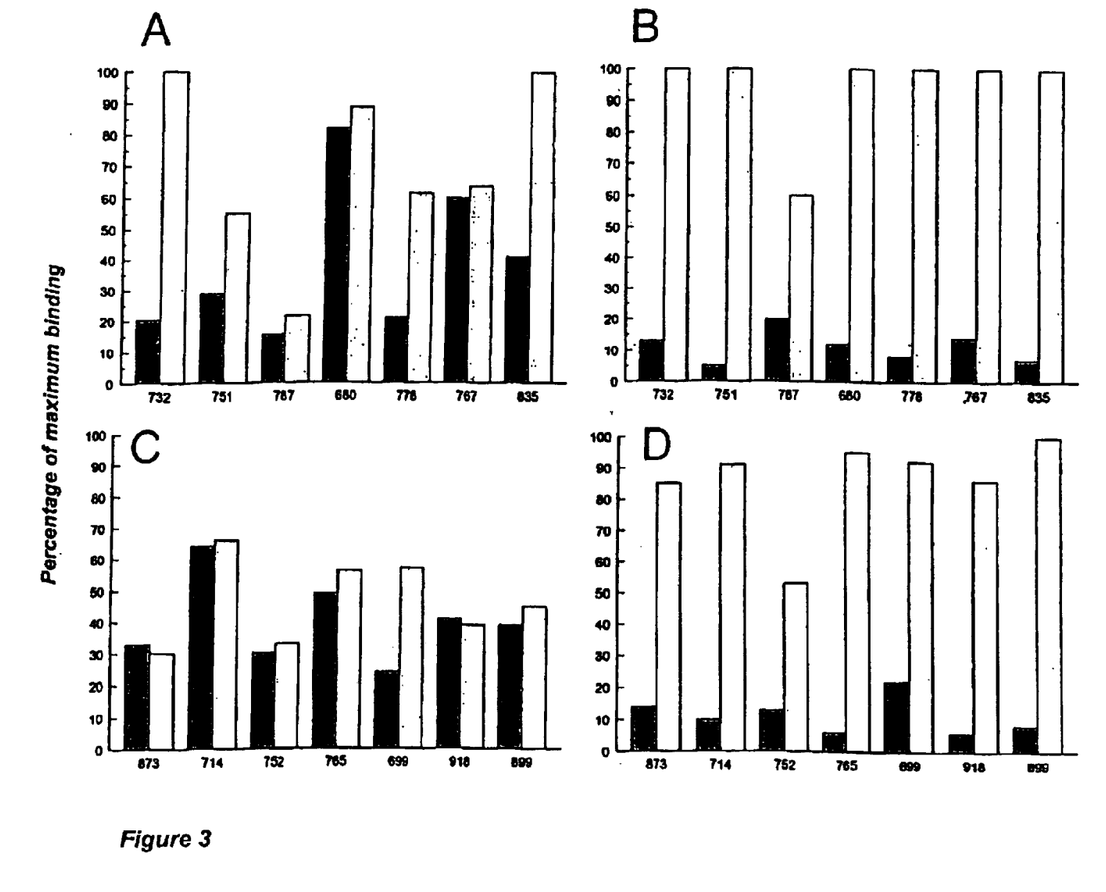
Figure 4:
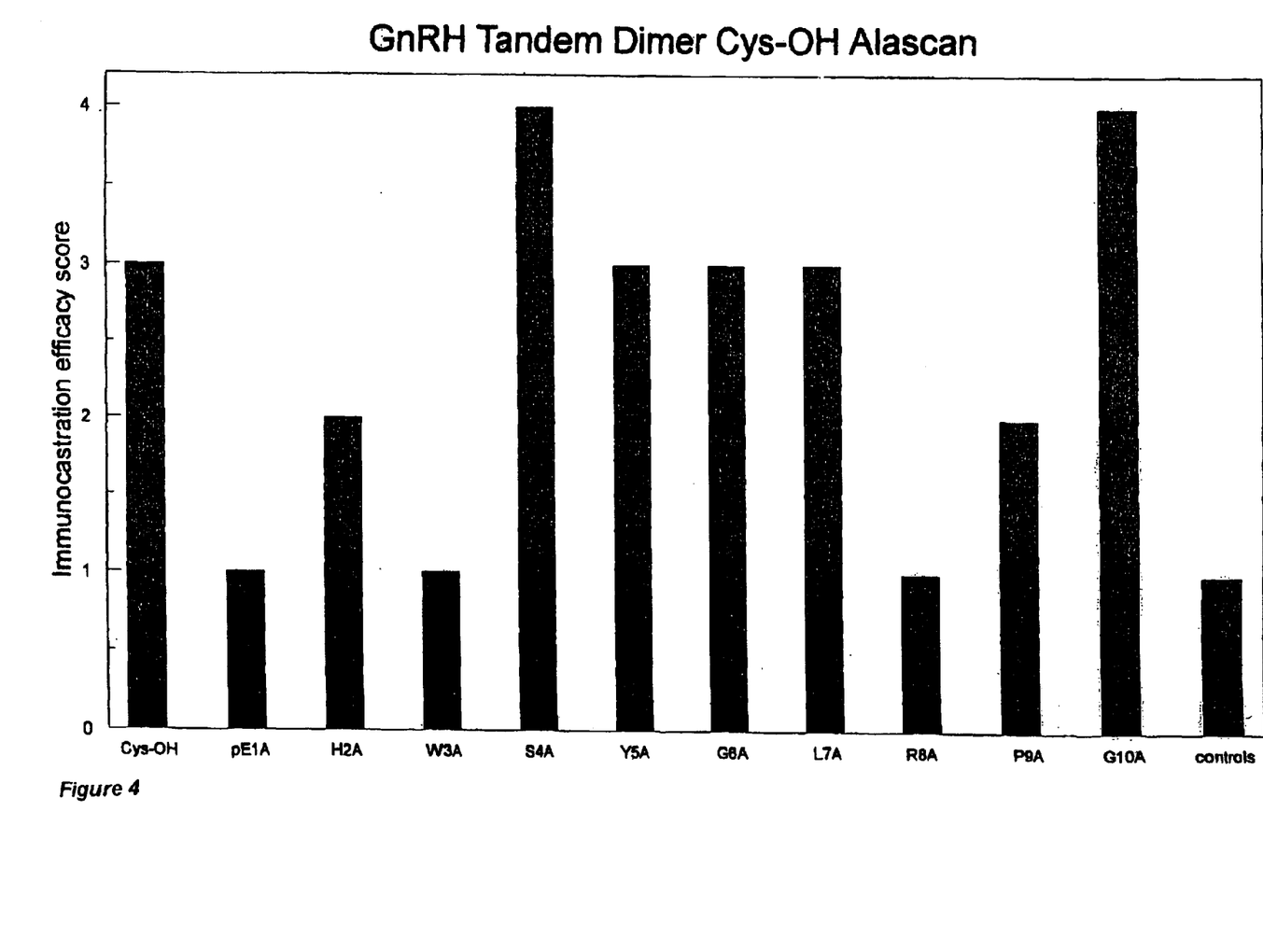
FIG. 4: Immunocastration efficacy score of several groups of pigs immunized with GnRH-tandem-dimer peptides (62 mg) conjugated to ovalbumine and Specol used as an adjuvant. The starting peptide was GnRH tandem (Cys-OH) dimer (abbreviated Cys-OH). Of this peptide all alanine scan peptides were used for immunization. Immunocastration efficacy was rated on a scale of 1 to 4(1=immunocastration did not occur, 2=a minority of the pigs were immunocastrated, 3=a majority of the pigs were immunocastrated, and 4=all pigs were immunocastrated).

The antibody binding results obtained with the pre-booster sera were different from the 10 wpv sera. Antisera of the pEIA and S4A treatments have been tested for their ability to recognize GnRH-I or GnRH-II (see FIG. 3). For both peptides 10 wpv sera from 6 out of 7 animals did not bind GnRH-II. Of the pE1A sera obtained before booster immunization 4 out of 7 animals showed binding to GnRH-II. Two sera did not recognize GnRH-II and one serum showed no binding to iodinated GnRH. The results of the S4A pre-booster sera are contradictory to the results of the 10 wpv sera. The pre-booster sera of all animals of the S4A group did recognize GnRH-II, with the inhibition of binding capacity of iodinated GnRH being similar for both GnRH-I and GnRH-II.

What is claimed is:

1. A peptide comprising a modified tandem GnRH decapeptide sequence capable of inducing an immunogenic response that allows for discrimination between different types of GnRH, said peptide selected from the group consisting of SEQ ID NO: 5, SEQ ID NO: 6, and SEQ ID NO: 7.

2. A vaccine comprising the peptide of claim 1.

3. The vaccine of claim 2, further comprising an adjuvant.

4. The vaccine of claim 3, wherein said adjuvant is an oil phase of an emulsion selected from the group consisting of a water-in-oil emulsion and a double oil emulsion.

5. The vaccine of claim 2 that is sufficiently active for administration in a single dose for the essential immunocastration of pigs.

6. A peptide comprising at least two modified tandem GnRH decapeptide sequences capable of including an immunogenic response that allows for discrimination between different types of GnRH, wherein said modified tandem GnRH decapeptide sequences are selected from the group consisting of SEQ ID NO: 5, SEQ ID NO: 6, and SEQ ID NO: 7.

7. A peptide comprising a tandem GnRH decapeptide, wherein said peptide is selected from the group consisting of SEQ ID NO: 5, SEQ ID NO: 6, and SEQ ID NO: 7.

8. A vaccine comprising the peptide of claim 7.

9. The vaccine of claim 8, further comprising an adjuvant.

10. The vaccine of claim 9, wherein said adjuvant is an oil phase of an emulsion selected from the group consisting of a water-in-oil emulsion and a double oil emulsion.

11. The vaccine of claim 8 that is sufficiently active for administration in a single dose for the essential immunocastration of pigs.

* * * * *

SEQUENCE LISTING

<160> NUMBER OF SEQ ID NOS: 13

<210> SEQ ID NO 1
<211> LENGTH: 10
<212> TYPE: PRT
<213> ORGANISM: Sus scrofa
<220> FEATURE:
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (10)..(10)
<223> OTHER INFORMATION: X=Gly-NH2

<400> SEQUENCE: 1

Xaa His Trp Ser Tyr Gly Leu Arg Pro Xaa
1               5                   10

<210> SEQ ID NO 2
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (10)..(10)
<223> OTHER INFORMATION: X=Gly-NH2

<400> SEQUENCE: 2

Xaa His Trp Ser His Gly Trp Tyr Pro Xaa
1               5                   10

<210> SEQ ID NO 3
<211> LENGTH: 20
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid or Gln with attached tail
      of one or more additional amino acids
<221> NAME/KEY: MISC_FEATURE
<222> LOCATION: (3)..(3)
<223> OTHER INFORMATION: X=Trp or N(indole)-formyl-tryptophan
<221> NAME/KEY: SITE
<222> LOCATION: (10)..(11)
<223> OTHER INFORMATION: there is either a direct bond or a spacer group
      between Gly at position 10 and Gln at position 11
<221> NAME/KEY: MISC_FEATURE
<222> LOCATION: (13)..(13)
<223> OTHER INFORMATION: X=Trp or N(indole)-formyl-tryptophan
<221> NAME/KEY: MISC_FEATURE
<222> LOCATION: (20)..(20)
<223> OTHER INFORMATION: X=Gly-NH2 or Gly with attached tail or one or
      more amino acids
<221> NAME/KEY: REPEAT
<222> LOCATION: (10)..(19)
<223> OTHER INFORMATION: repeat of amino acid sequence between positions
      10-19 where the amino acids in positions 10-19 are present at
      least once

<400> SEQUENCE: 3

Xaa His Xaa Ser Tyr Gly Leu Arg Pro Gly Gln His Xaa Ser Tyr Gly
1               5                   10                  15

Leu Arg Pro Xaa
            20

```
<210> SEQ ID NO 4
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 4

Xaa His Trp Ser Tyr Xaa Leu Arg Pro Gly Xaa His Trp Ser Tyr Xaa
1               5                  10                  15

Leu Arg Pro Gly Xaa
            20

<210> SEQ ID NO 5
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: D-Lys
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 5

Xaa His Trp Ala Tyr Xaa Leu Arg Pro Gly Xaa His Trp Ala Tyr Xaa
1               5                  10                  15

Leu Arg Pro Gly Xaa
            20

<210> SEQ ID NO 6
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
```

-continued

```
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys=NH2

<400> SEQUENCE: 6

Xaa His Trp Ser Tyr Xaa Leu Ala Pro Gly Xaa His Trp Ser Tyr Xaa
1               5                   10                  15

Leu Ala Pro Gly Xaa
            20

<210> SEQ ID NO 7
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 7

Xaa His Trp Ser Tyr Xaa Leu Arg Pro Ala Xaa His Trp Ser Tyr Xaa
1               5                   10                  15

Leu Arg Pro Ala Xaa
            20

<210> SEQ ID NO 8
<211> LENGTH: 42
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=NH2-Glu
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (22)..(22)
<223> OTHER INFORMATION: X=NH2-Glu
<221> NAME/KEY: MISC_FEATURE
<222> LOCATION: (27)..(27)
<223> OTHER INFORMATION: X=D-Lys
<221> NAME/KEY: MISC_FEATURE
<222> LOCATION: (32)..(32)
<223> OTHER INFORMATION: X=Gln or Gln preceded by a spacer
```

```
<221> NAME/KEY: MISC_FEATURE
<222> LOCATION: (37)..(37)
<223> OTHER INFORMATION: X=D-Lys
<221> NAME/KEY: SITE
<222> LOCATION: (21)..(42)
<223> OTHER INFORMATION: dimer formed between Cys 21 and Cys 42

<400> SEQUENCE: 8

Xaa His Trp Ser Tyr Xaa Leu Arg Pro Gly Xaa His Trp Ser Tyr Xaa
1               5                   10                  15

Leu Arg Pro Gly Cys Xaa His Trp Ser Tyr Xaa Leu Arg Pro Gly Xaa
            20                  25                  30

His Trp Ser Tyr Xaa Leu Arg Pro Gly Cys
        35                  40

<210> SEQ ID NO 9
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 9

Xaa His Trp Ser Tyr Xaa Leu Arg Pro Gly Xaa His Trp Ser Tyr Xaa
1               5                   10                  15

Leu Arg Pro Gly Xaa
            20

<210> SEQ ID NO 10
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=Ala modified with acetyl group
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 10

Xaa His Trp Ser Tyr Xaa Leu Arg Pro Gly Ala His Trp Ser Tyr Xaa
1               5                   10                  15

Leu Arg Pro Gly Xaa
            20
```

```
<210> SEQ ID NO 11
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (11)..(11)
<223> OTHER INFORMATION: X=Gln or Gln preceded by a space
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 11

Xaa His Trp Ser Ala Xaa Leu Arg Pro Gly Xaa His Trp Ser Ala Xaa
1               5                   10                  15

Leu Arg Pro Gly Xaa
            20

<210> SEQ ID NO 12
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
<221> NAME/KEY: MISC_FEATURE
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 12

Xaa His Trp Ser Tyr Xaa Ala Arg Pro Gly Xaa His Trp Ser Tyr Xaa
1               5                   10                  15

Ala Arg Pro Gly Xaa
            20

<210> SEQ ID NO 13
<211> LENGTH: 21
<212> TYPE: PRT
<213> ORGANISM: Artificial Sequence
<220> FEATURE:
<223> OTHER INFORMATION: A peptide suitable for eliciting an immune
      response against forms GnRH/ LHRH.
<221> NAME/KEY: MISC_FEATURE
<222> LOCATION: (1)..(1)
<223> OTHER INFORMATION: X=pyroglutamic acid
<221> NAME/KEY: MISC_FEATURE
<222> LOCATION: (6)..(6)
<223> OTHER INFORMATION: X=D-Lys
<221> NAME/KEY: MISC_FEATURE
```

```
<222> LOCATION: (11)..(11)
<223> OTHER INFORMATION: X=Gln or Gln preceded by a spacer
<221> NAME/KEY: MISC_FEATURE
<222> LOCATION: (16)..(16)
<223> OTHER INFORMATION: X=D-Lys
<221> NAME/KEY: MISC_FEATURE
<222> LOCATION: (21)..(21)
<223> OTHER INFORMATION: X=Cys-NH2

<400> SEQUENCE: 13

Xaa His Trp Ser Tyr Xaa Leu Arg Ala Gly Xaa His Trp Ser Tyr Xaa
1               5                   10                  15

Leu Arg Ala Gly Xaa
                20
```